United States Patent [19]
Kimmel et al.

[11] Patent Number: 6,112,903
[45] Date of Patent: Sep. 5, 2000

[54] CULLET SORTING BY DIFFERENTIAL THERMAL CHARACTERISTICS

[75] Inventors: Kevin S. Kimmel, Brandon, Fla.; Neal A. Hawk, Dresden, Ohio

[73] Assignee: Eftek Corporation, Berlin, N.J.

[21] Appl. No.: 08/915,106

[22] Filed: Aug. 20, 1997

[51] Int. Cl.$^7$ ................ B03B 1/00; B07B 5/00; B07C 47/31
[52] U.S. Cl. .............. 209/11; 209/577; 209/639; 198/461.2
[58] Field of Search .................. 209/3, 11, 576, 209/577, 587, 656, 657, 638, 639, 938, 939; 198/461.2

[56] References Cited

U.S. PATENT DOCUMENTS

| | | | |
|---|---|---|---|
| 4,933,075 | 6/1990 | Nordin et al. | 209/576 |
| 5,124,662 | 6/1992 | Downing et al. | 324/636 |
| 5,161,695 | 11/1992 | Roos | 209/11 |
| 5,209,355 | 5/1993 | Mindermann | 209/3.1 |
| 5,429,246 | 7/1995 | Kaiser et al. | 209/3.1 |
| 5,558,199 | 9/1996 | Roether et al. | 198/461.2 |
| 5,628,409 | 5/1997 | Thomas | 209/577 |

OTHER PUBLICATIONS

Reprint, "2 to 18 GHz Broadband Microwave Heating Systems," *Microwave Journal*, Nov. 1993.
"Microwave Laboratories'CEO Receives Advanced Technology Award," *PR Newswire*, Mar. 9, 1993.
"Materials Processing with Microwave Energy," *Mechanical Engineering —CIME*, 117:8, p.102, Aug. 1995.
"Re: Efficient recycling collection," *Resource Recycling*, Jul. 17, 1995.
"Montgomery County Recycling Guide," Montgomery County, PA Oct. 1995.

*Primary Examiner*—Donald P. Walsh
*Assistant Examiner*—Brett C. Martin
*Attorney, Agent, or Firm*—Duane, Morris & Heckscher LLP

[57] ABSTRACT

A stream of mixed particulates of two or more materials having different induction heating characteristics (i.e., distinct thermal, dielectric strength and/or loss tangent characteristics), such as recycled glass cullet including fragments of glass mixed with fragments of glass-like contaminants such as ceramics, pyroceramics, tempered glass or the like, is sorted using the differing characteristics of the glass and contaminants to cause detectable differences in temperature. A thick heating layer many particles deep is formed on a conveyor path for heating the stream in a compact mass for uniform heating. An electromagnetic induction heater applies microwave energy between 0.915 and 2.45 GHz for heating the mass, which is then spread into a thin detecting layer, for example one particle deep, on a further conveyor. The detecting layer is digitally imaged using a thermal camera. The thermal image data is analyzed for temperature differences, particularly for temperature differences from an average temperature computed for discrete lateral lanes. A downstream diverter mechanism is triggered to divert incremental portions of the material stream found to contain temperature differences, thereby removing the contaminants.

24 Claims, 4 Drawing Sheets

CULLET SORTING BY DIFFERENTIAL THERMAL CHARACTERISTICS

BACKGROUND OF THE INVENTION

1. Field of the Invention

The invention relates to bulk material sorting methods and apparatus, and in particular to sorting materials such as particulate recycled glass by heating a conveyed stream of particles using microwave induction heating and then discriminating for particles at different temperatures. Microwave energy, preferably in the frequency range of 0.915 to 2.450 GHz, differentially heats glass cullet particles of different compositions due to their differing thermal characteristics, dielectric strengths and loss tangents. The different compositions that are sorted can comprise glass particles having different melting temperatures such as borosilicate glass vs. pyroceramics. The heated cullet is discriminated and sorted by capturing and analyzing pixel image frames from a thermal imaging camera, including separately analyzing laterally adjacent lanes in the image frames. Thermal image data captured by the camera is used to control one or more mechanisms operable to divert materials having a detected temperature different from an average temperature of the stream of cullet in each lane, thereby separating out or concentrating predetermined materials. The invention is particularly useful for separating ceramic contaminants from recycled glass as well as metals.

2. Prior Art

Municipalities routinely collect glass for recycling; however even after substantial washing and sorting steps, the composition of the collected glass is not uniform. Processors attempting to use the recycled glass find, for example, that some of the glass particles melt at a higher temperature than others, which leads to processing problems that render the recycled material unsuitable for certain uses. Recycled glass materials comprise containers and broken glass pieces that are clear (or "flint") or colored, typically amber or green. When collected for recycling, various non-glass contaminant materials are present. Non-glass contaminants having physical properties that are distinctly different than those of the glass can be sorted out by discriminating for differences in properties. For example, metal bottle caps and the like can be removed during crushing and screening steps because metal is malleable and is flattened by crushing, but glass is frangible and breaks into small pieces that can be screened. Ferromagnetic metals can be removed magnetically. Contaminants such as organics, dirt, paper from labels and the like can be removed by washing, rinsing and filtering steps. Plastics are generally less dense than glass and can be removed by rinsing, skimming or winnowing steps.

A greater problem is confronted in attempting to sort out materials that have properties that are quite similar to those of glass. Occasional pieces of ceramics, pyroceramics (e.g., Corning Corelle ware), tempered glass (e.g., Corning Pyrex glass), stones and other materials are frequently present in the recycled cullet. These contaminants are not readily distinguishable from glass by their physical properties, which in many respects resemble the properties of glass. Most sorting techniques are not effective to detect and remove them because their physical, electrical and chemical properties are substantially the same as those of glass. Recycling authorities accordingly may instruct consumers to recycle only glass food and beverage containers, and not (for example) glassware, crystal, ceramics, plate glass, mirrors and the like. Inevitably some of these materials find their way into recycled glass.

Contaminants can cause difficulties in processing cullet into new glass. The recycling process typically includes comminuting the glass into relatively small particles that are processed in bulk. Particles that have properties that are distinct from those of the other particles represent defects in the bulk material. For example, ceramics and tempered glass have a higher melting temperature than glass, such that they may not melt completely and/or mix homogeneously in remelted glass. The result may be localized defects in molded recycled glass, clogging of spinnarettes used to make fiberglass from recycled glass, and other problems. For these reasons, recycled glass may be relegated to uses taking negligible advantage of its properties, such use as a filler in paving material. On the other hand, it is impractical or impossible to manually pre-sort cullet effectively before comminution or breakage.

Many types of materials are recycled, such as glass, plastic, paper and metals, often in mandatory programs intended to reduce waste and conserve landfill space. A municipality may require that recycled materials be sorted manually into different containers that are dumped into different receptacles upon collection. More often, there are too many categories to justify segregation of each variety of material through the process. Typically glass, plastic and metal are collected together for later sorting. Even if an attempt is made to sort by material, consumers cannot be expected to be sensitive to a difference in types of glass, and may commingle distinct materials inadvertently.

Recyclables collected in commingled collection programs need to be sorted during further processing if a relatively pure material is needed, for example to make new glass containers or the like from the recycled ones. Manual sorting is possible but tends to be prohibitively expensive, and the most careful sorting can be ineffective when much of the glass is broken. Due to the inability to sort types of glass and to separate glass and non-glass materials, recycled glass cullet often is not used to make new glass, and is substantially less valuable than material that is more pure. For example, recycled glass cullet of moderate particle size may be used as an aggregate or filler in roadway paving. Smaller particles may be used as "sand" for golf course bunkers. Although these uses are not insubstantial, the economic and product purity issues are such that approximately 85% of recycled mixed cullet goes into landfills.

There can typically be up to 10% contaminants in recycled glass material, i.e., 200 lbs. per ton. It would be advantageous if recycled glass could be sorted more effectively to remove non-glass materials. This problem is acute with respect to ceramics, pyroceramics and tempered glass, which resemble glass in many of their properties.

In addition to avoiding waste of material, glass cullet liquifies at a lower temperature than new glass batch, and has favorable viscosity characteristics. Less heat energy is necessary to melt cullet than new batch, reducing costs and environmental emissions. Processing time is reduced, improving productivity. It would be advantageous to use recycled glass to make new glass containers, fiberglass and other products in order to conserve resources and reduce costs.

For all these reasons, it would be advantageous to provide a more practical technique to distinguish and sort glass and non-glass materials having properties similar to glass, which can be operated on a production scale. The present invention provides a method and means for distinguishing among various contaminant materials by taking advantage of their different thermal characteristics with respect to rates of heating and/or cooling and their distinct dielectric strengths and loss tangents, which produce different temperatures when subjected to the same electromagnetic radiation and handling conditions. The invention uses a mass heating technique to maximize temperature differences in a particulate stream, redistributes the heated particulates, and analyzes their thermal image in distinct sections, for rendering hot and/or cool spots detectable and easily diverted from the stream.

SUMMARY OF THE INVENTION

It is an object of the invention to distinguish between glass and non-glass contaminant materials found in glass cullet, by employing different heat induction properties of glass particles and contaminants, especially ceramics, pyroceramics and tempered glass but also other potential contaminants.

It is another object of the invention to heat the mixture of glass particles and contaminant particles, and to distinguish between the two based on a resulting difference in residual temperature that occurs after heating the mixture so as to enable detection of contaminants.

It is a further object to maximize the effects of distinct heating and cooling characteristics of the glass particles and contaminants.

It is another object to provide a temperature sensor along a conveyor having at least one and preferably a plurality of diverters operable under control of the temperature sensor to divert selected portions of a stream of material moving along the conveyor.

It is another object to adjust contrast scaling and to develop different setpoint criteria for discrete areas of the conveyed stream of material, especially in lateral sections or lanes in the stream.

These and other objects are accomplished by an apparatus and method for sorting a stream of mixed particulates of at least two distinct materials having different induction heating characteristics, especially different rates of heating and/ or cooling in glass cullet having particulate glass mixed with contaminants such as pieces of ceramics, pyroceramics, tempered glass, stones and metals.

The unsorted particulate material is collected in a thick mass on a conveyor moving the material along a heating and detection path, namely in a layer that is a plurality of particle thicknesses deep and wide, e.g., approximately three inches (7.6 cm) deep and three feet (1 m) wide, composed of materials ranging up to 1 cm on a side. An electromagnetic induction heater is disposed along the heating path and applies an alternating electromagnetic field to heat the stream of mixed particulates. The field is preferably relatively low, single frequency microwave energy but can also comprise a plurality of frequency components, swept or chirped through a frequency range, to reduce localized hot spots and to reduce sensitivity to coupling between the field generating circuits and the materials being heated. A plurality of induction heaters can be provided and operated to heat the material sequentially using different frequencies or frequency ranges. As another alternative, waveguides and chopper blades can be employed to apply the energy evenly.

Microwave energy is applied in a frequency range of 0.915 to 2.450 GHz, preferably 0.915 GHz. The field is applied over a time sufficient to develop a detectable temperature differential Δt, e.g., in the range of 2.5° C. to 12° C., preferably 6° C. or more. The heating of the material is maximized by the mass of the material when the induction heating energy is applied.

The heated cullet is then spread, preferably to a thickness of only one particle. Preferably this is accomplished by transferring the mass of plural-thickness material promptly after being conveyed through a heating zone, to a second conveyor defining the detecting part of the path. The detecting path conveyor is moved faster than the heating path, thereby effectively spreading the heated cullet into a relatively thin stream of the mixed particulates along the detecting path.

At least one temperature sensor is disposed along the detecting path, and can include an infrared imaging sensor, a plurality of discrete sensors, a movable sensor or the like. The temperature sensor(s) detect the temperature of discrete fragments or localized portions of the stream and produce a signal identifying temperature differences. For example, the detected heat distribution pattern is digitized and mapped for two dimensional frames encompassing sections of the passing stream. This data is analyzed by a processor to identify portions of the stream having a temperature above and/or below predetermined setpoint limits, such as areas whose temperature is distinctly greater than or less than an average detected temperature. The temperature sensor signal marks fragments or portions of the cullet stream that contain materials other than glass, such as ceramic, pyroceramics, tempered glass and/or metal contaminants which become detectably hotter or cooler than glass.

At least one controllable diverting mechanism is responsive to the signal of the temperature sensor, and diverts the marked fragments or portions from the detecting path, thereby separating the two materials, and in particular removing contaminant materials while passing purified glass cullet. A variety of specific diverter mechanisms can be employed such as solenoid operated air valves to blow material from the stream, or gates that open or close to separate the material.

The heat mapping signal can be developed by scanning with a non-contact temperature sensor such as a pyrometer coupled to a control computer. The computer is likewise coupled to a shaft encoder or drive motor associated with the conveyors, for coordinating operation of the diverting mechanism at the appropriate time to divert material from the advancing cullet stream. Preferably, however, a thermal imaging camera captures repetitive frames of image data, which is digitized and treated by the processor as data representing distinct laterally adjacent lanes in the material. The processor can scale the data to maximize the resolution of the data from the thermal imaging camera over a selected temperature range such as a range only slightly wider than the maximum and minimum temperatures encountered. The processor likewise can analyze successive frames showing the same particles advancing over time for averaging or time variant criteria, maintain variable setpoints as well as different setpoints for each lane to account for variations over time and for the tendency of material at the edges of the stream to cool more quickly than material near the center, and otherwise operate on the data to enhance effective contrast and dependability of detection.

Additional aspects and objects of the invention will be apparent in connection with the following discussion of practical examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

Figure 1:
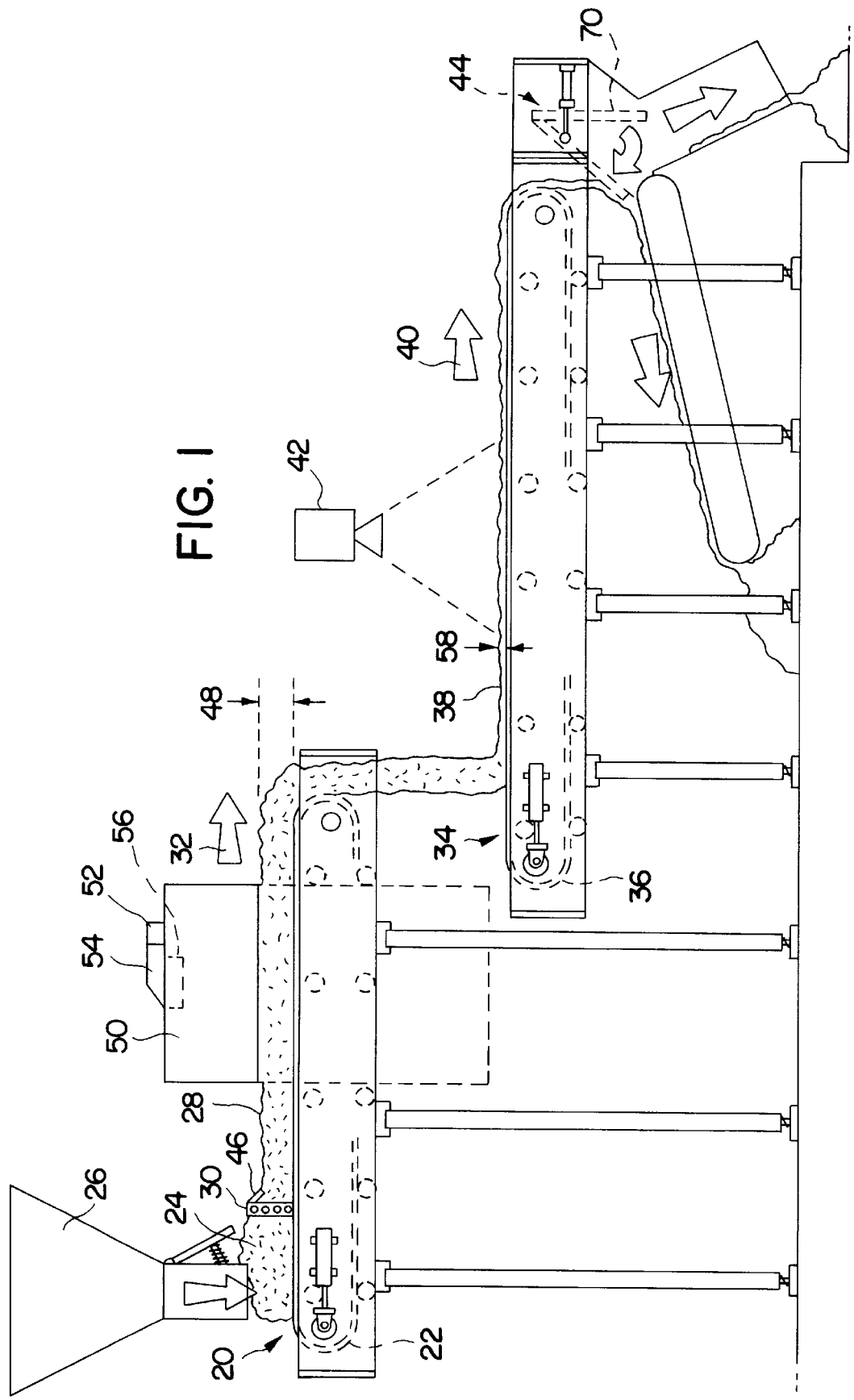
FIG. 1 is a schematic elevation view showing elements of the apparatus of the invention according to one embodiment.

As shown generally in FIG. 1, cullet sorting according to the invention can be accomplished using a first conveyor 20 having an electrically non-conductive endless belt 22 for carrying cullet 24. The cullet is loaded in a thick heating layer, for example being released from a hopper 26 and spread uniformly in a relatively thick layer 28 with a cullet rake 30 or the like. This layer 28 is preferably many particles thick such that the material forms a substantial thermal mass or electromagnetic and/or thermal sink. The first conveyor 20 moves layer 28 along a horizontal heating path through a microwave heater 50, which heats the material by electromagnetic induction heating, and due to the thermal mass of layer 28, to some extent by conduction, convection and radiation from other particles. This produces a relatively uniform application of energy to the individual particles.

The stream of heated cullet moves in the direction of arrow 32 and is spread thinly, preferably to a depth of single particles, for example being transferred to a second and faster horizontal conveyor 34 having an endless belt 36 for carrying the heated cullet along a horizontal detecting path shown by arrow 40. The heated cullet as spread into a relatively thin detecting layer 38 is carried on conveyor 34 through the field of a temperature sensor such as an infrared camera 42, which captures one or more thermal images of each passing particle. The image signal from camera 42 is digitized and defines a pixel field analyzed by an associated processor (not shown in FIG. 1) to detect localized differences in temperature that represent different materials contained in the cullet. A diverting mechanism 44 responsive the processor, and ultimately the temperature sensor signal, is located downstream of temperature sensor 42 such that selected portions of the cullet material are diverted from the conveying path, thereby separating contaminants from the cullet.

Typical recycled glass cullet mostly comprises particulate glass fragments from food and beverage containers, with occasional contaminants. The invention is applicable to sorting glass in any size from unbroken containers to crushed particles, but is discussed herein with respect to crushed cullet particles of clear (flint), amber and/or green glass, with interspersed contaminant particles such as ceramics, pyroceramics, tempered glass and the like, having thermal characteristics, dielectric strengths and loss tangents that are distinct from those of regular cullet glass, substantially borosilicate glass.

The cullet is generally pre-processed prior to loading into the hopper 26. Appropriate pre-processing includes, but is not limited to, crushing and screening, separation of low density material, magnetic and metal separation, washing, rinsing, drying, segregation by particle size, etc. In order to minimize the energy consumed during microwave heating, washed cullet is generally dried using a forced hot air oven using a gas or oil fired heat source. After drying, the cullet has a pre-heating temperature due to the residual heat from the drying process. It has been determined that the pre-heating temperature of the washed and dried cullet has an effect on the subsequent microwave heating process. Generally a pre-heating temperature in the range of 60° C. to 82° C. provides the largest resulting temperature differences between the glass particles and contaminants in the cullet after microwave heating.

The first conveyor 20 is driven by a motor (not shown) and moves with a heating path velocity in the direction of arrow 32. Cullet material is discharged from hopper 26 and moves left to right as shown in FIG. 1. The cullet material 24 is spread across the surface of the first conveyor in a relatively thick heating layer 28 by passing under a cullet rake or gate 30, for example with a horizontally pivoted flap 46 biased by gravity or by a spring (not shown) to rest adjacent to the conveyor surface. The cullet rake 30 spreads the cullet material 24 laterally on the first conveyor 20 thereby defining a heating layer mass having a thickness 48. For best results, the heating layer thickness is approximately three inches (7.6 cm). The conveyor can likewise be about three feet (1 m) wide, although other widths are possible.

The heating layer 28 is carried by the first conveyor 20 into the cavity of a microwave heating system 50 that encompasses belt 22 of first conveyor 20. A single microwave heater is shown in the present embodiment and is preferable in order to minimize cost. The microwave heater includes a klystron tube 52, a waveguide 52 and a motor driven stirrer 56 (motor not shown) for even distribution of microwave energy. Alternatively duel microwave heaters can be used for increased capacity. The microwave heater is preferably operated at a relatively low single frequency (i.e., 0.915 GHz), and can comprise a klystron tube or a gyrotron or similarly resonant microwave generating device, coupled for example by a waveguide to direct electromagnetic energy into the layer of particulate material.

The invention is also applicable to a microwave systems operable at multiple frequencies or systems in which the microwave frequency is swept or chirped over a range encompassing one or more frequencies. A broad band microwave heating system using a high power traveling-wave tube amplifier and a highly over-moded applicator cavity is available from Microwave Laboratories, Inc. of Raleigh, N.C., and is suitable for use according to the invention. With a single travelling wave tube, a useful bandwidth of an octave or more is possible, and by using a second tube or a second microwave heater as shown, the bandwidth can be expanded. Nevertheless, a single relatively low frequency microwave is preferred because higher frequency devices are relatively expensive.

Microwave heating differs from conventional convection and radiation heating in that electromagnetic energy penetrates and propagates in the materials being heated and generates heat by translating ionic and molecular dipoles in the material. Electromagnetic resonance on this level is therefore determined by the materials and their constituent atoms and molecules. Ceramics comprise sintered silica, which is more crystalline than amorphous glass. Ceramics also include constituents or constituent proportions not found in glass, that are resonant at distinct frequencies, enabling selective heating.

It has been determined that acceptable differential heating can be achieved by applying single frequency microwave energy to a relatively thick heating 28 layer of cullet. The microwave generator can be high powered or low powered, depending on the length of time the material is exposed. The heating layer is preferably three feet wide (91 cm) and with a heating layer thickness 48 of three inches (7.6 cm). Heating, for example, at 1 KW requires application of power for 1 to 1.5 minutes to develop a temperature difference between glass and ceramics of 5 to 12° C., which is readily detectable with a thermal imaging camera.

Upon exiting the microwave heating system 50 along the conveying path, the cullet fragments in the heating layer begin to cool by radiation and convection. To some extent, the rate of cooling also depends on different thermal characteristics of the materials. The heating layer is transferred onto the second conveyor 36 driven by a motor (not shown) and moving with a detecting path velocity. Preferably the detecting path velocity is 4.5 to 15.5 times greater than the heating path velocity. The increased velocity of the detecting path allows caused the heated cullet particles to spread into a relatively thin detecting layer having a detecting layer thickness 58, that is optimally one particle thick.

The second conveyor can comprise a vibratory conveyor section which simultaneously spreads and conveys the heated cullet while settling the particles into an even layer of single particle thickness. The second conveyor can be wider than the heating path and/or moved faster than the heating path velocity to cause adequate spreading of the detecting layer, such that an undue proportion of the particles are not obscured. Thus the preferred detecting layer thickness 58 is approximately equal to the average particle size of the cullet material (e.g., 1 to 1.6 cm). The relatively thin detecting layer 38 allows for very precise thermal imaging, detection of temperature differences between individual particles and the average temperature, and accurate separation of contaminants from the detecting layer.

Figure 2:
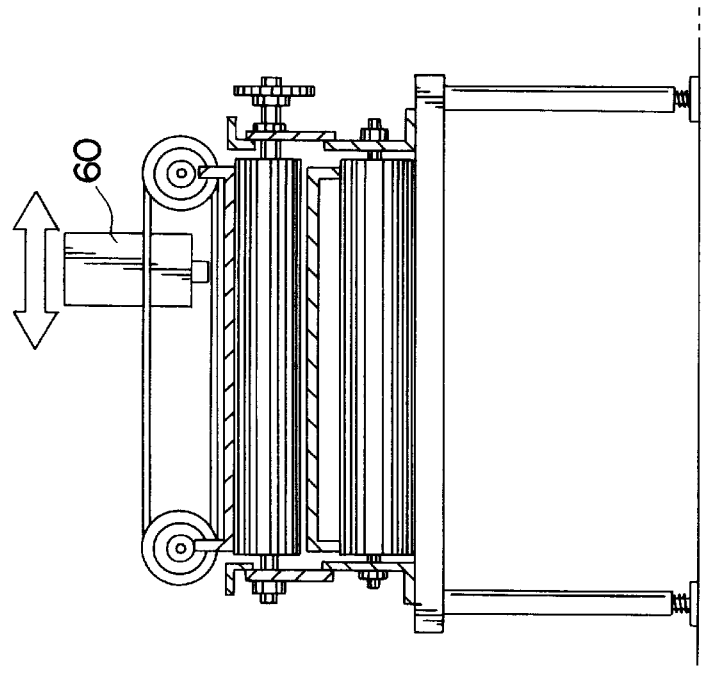
FIG. 2 is an end elevation view showing an oscillating form of scanning temperature sensor.

A temperature sensor located along the detecting path 40 senses the temperature of the particles in the detecting layer 38 moving along the second conveyor 34. FIG. 1 shows a fixed imaging temperature sensor in the form of an infrared camera 42, which captures successive frames of image data. FIG. 2 is an end elevation view showing an alternative scanning temperature sensor 60 arranged to pass laterally over the cullet stream in oscillating passes. In any case, the cullet fragment temperatures are sensed for detecting temperature differences, at least for discrete lanes or longitudinally extending sections of the cullet stream and preferably for discrete longitudinal and lateral areas. The temperature sensor provides a signal that can be processed by threshold comparison or the like to discriminate areas having different temperatures. The signal, or the result of processing of the signal, is stored or recorded and used to trigger later operation of a diverting mechanism 44 located downstream of temperature sensor such that selected portions of the cullet material are diverted from the detecting path 40, for example diverting the cullet at hotter or cooler areas considered to contain metals, tempered glass, pyroceramics or other materials whose temperature is found to differ from the intermediate temperature of passable glass cullet, for example of borosilicate glass.

Temperature sensor 42 in the embodiment of FIG. 1 preferably comprises an infrared camera 42 having an infrared CCD array and scalable digitizer operable to capture and store thermal image data. A suitable infrared camera is the Amber SENTINEL, which is an uncooled, microbolometer-based infrared imaging system, available from Amber, Inc. of Goleta Calif. Infrared camera 42 can have a resolution of 320×240 pixels and is operable at a full video rate of 30 frames per second. The infrared camera generally has an integrated circuit based two dimensional array of infrared-responsive elements upon which the thermal image of the cullet material is focused by suitable optics (not shown). The thermal image data captured by the array is used to generate a two dimensional video image at up to 30 frames per second. The successive frames of thermal image data can be compared with threshold limits by analog or preferably-digital means to develop a two dimensional bitmap, representing the spatial position of cullet fragments that are sensed to have at least two distinct temperatures or a difference in temperature from one or more calculated averages such as the frame average, a running average or preferably a local-area average over an area large enough that the average is not unduly skewed by contaminants. A combination of such analyses can be made. The fragments at the respective levels are thus distinguished as glass or contaminants based upon their temperatures. These analyses can be processed for distinct contrasting temperatures up to the pixel resolution of the camera, or for larger areas that correspond to the minimum lateral and longitudinal dimensions of a divertable portion of the cullet stream. Preferably the data is processed up to the pixel resolution of the camera to best respond to individual contaminant particles, using average temperatures specific to individual longitudinally extending laterally adjacent lanes, for making an accept/reject decision as to each minimum-size divertable zone in the stream. The selection can be more or less stringent depending on the purity specifications required for the resulting product. Previously-processed cullet can be reprocessed in subsequent attempts to better remove and concentrate the contaminants. Likewise, previously-rejected cullet can be reprocessed in an effort to recover good cullet particles that were rejected due to the presence of adjacent contaminant particles.

In the embodiment of FIG. 2, temperature data of a similar nature can be obtained by using a movable sensor such as pyrometer 60, which is an alternative means to sense and preferably digitize the temperature of discrete areas of the cullet stream. According to this embodiment, the temperature sensor has a narrow field of view and is passed laterally over the cullet stream in successive raster-like passes to develop a temperature profile or two dimensional bitmap representing the position of glass and contaminant fragments, respectively.

Figure 3:
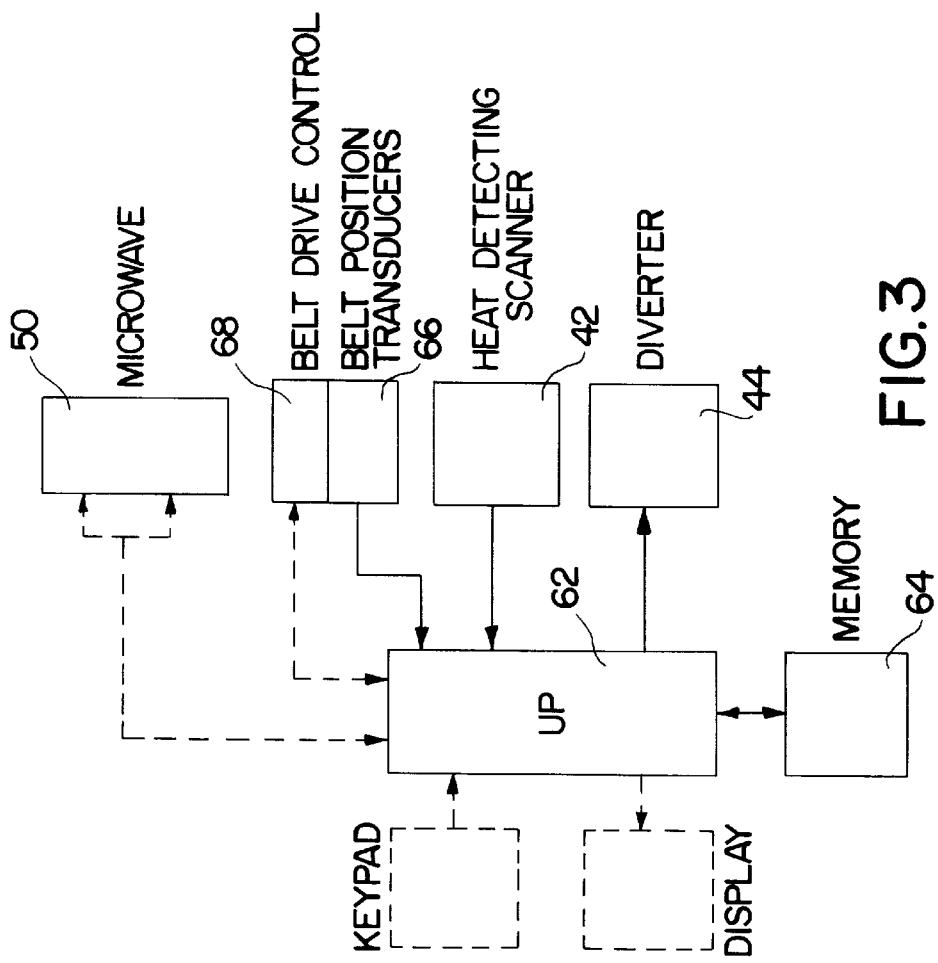
FIG. 3 is a block diagram showing sensing and control aspects of the invention.

Sensing and control aspects of the invention are shown in FIG. 3. A microprocessor controller 62 is coupled to the infrared camera 42 or temperature sensing scanner and records thermal image data for a predetermined portion of the cullet stream, which data is stored in a memory 64 coupled to microprocessor 62. The stored data is indexed in memory 64 to refer to particular locations along the moving cullet stream. For this purpose, microprocessor 62 is coupled to belt position transducers 66, for example comprising a shaft encoder. Alternatively, the advance of the heating and/or detecting path belts is determinable by virtue of operation of the belt drive control 68, such as using a stepping motor. For belts run at a constant speed, indexing can be accomplished as a function of timing, which is then converted to belt position information. In any event, the temperature data stored is referenced in memory to a particular place on the cullet stream which will be diverted or not diverted as a function of temperature when the corresponding section of material reaches the diverting mechanism.

As noted above, the individual data points collected can be an average temperature value taken at successive intervals during passage of the heated cullet stream, thereby collecting a linear succession of longitudinal pass-or-divert indicating values. If a scanning sensor, transverse linear image sensor or two dimensional image sensor arrangement is used, the data can represent a two dimensional array of temperature values used to make pass-or-divert decisions. The form of data output generally depends on the form of controllable diverter mechanism coupled to microprocessor 62 for diverting portions of cullet found to be distinct in temperature and thus likely contaminated. However, it is also possible to generate and store general process control information such as selection percentages over time, etc.

With reference to FIG. 1, the diverter can comprise a controllable diverting gate or flap 70 operable to divert the full lateral width of the cullet stream over a longitudinal distance of the stream corresponding to a distance found to be contaminated, which is appropriate if the data is collected and stored to represent longitudinal pass/divert information for successive increments of the cullet stream. Such an arrangement is likely to divert a substantial quantity of glass together with any contaminants therein, but nevertheless concentrates the contaminants and remove them from the stream of purified glass cullet that passes on through an outlet chute.

Figure 4:
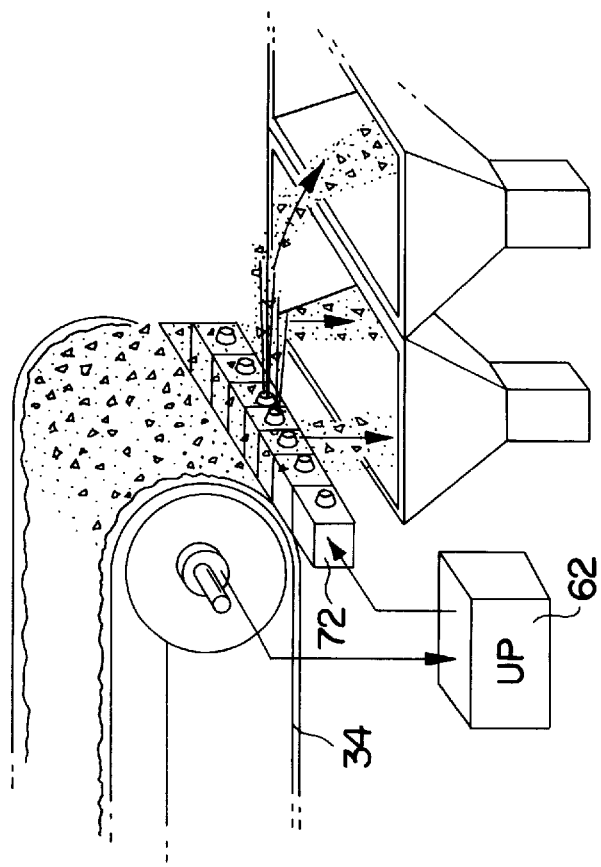
FIG. 4 is a schematic illustration of an alternative embodiment employing a variant form of diverter.

For the higher resolution situation in which a temperature measurement is made for each of a plurality of points across the lateral width of the cullet stream, whether by scanning or by two dimensional imaging, a plurality of diverters can be provided and controlled independently, each being operable to divert only a portion of the lateral width of the cullet stream. These diverters can comprise a plurality of short lateral diverting flaps as in FIG. 1. FIG. 4 shows an alternative embodiment in which the diverters comprise solenoid valves 72 coupled to a compressed air source 78 (FIG. 6) and controlled by microprocessor 62 to open close thereby providing a pulsed air stream operable to direct a stream of air at a point where the stream of cullet falls vertically from the end of the second conveyor 36, for diverting contaminants from the falling cullet stream into a collection area. Other forms of diverters such as trap door arrangements are also possible as will be apparent from the foregoing examples.

Preferably the thermal image data is divided into a plurality of distinct lanes 74 (FIG. 6) which are parallel to the detecting path 40. Operation of the data collection, data storage and diverting mechanisms can be coordinated with advance of the conveyor belts in a clocking or shift register fashion based on signals from the belt position transducers 66 or belt drive control 68. Alternatively, operation of the diverted is delayed by a time period corresponding to the delay for particular material to advance to the diverter. The belt position indicator can output a pulse for each incremental advance of the belt, triggering microprocessor 62 to load and store the data present on the temperature sensor output signal, and also triggering microprocessor 62 to advance by one increment in memory to access the data on the next incremental portion of the cullet stream to reach diverter mechanism 74. The resolution of the increments can be down to the size of individual cullet fragments, or a larger area of the cullet stream can be defined as one temperature area or pixel and one potentially divertable portion of the cullet stream.

Optional additional aspect of the invention are shown in FIG. 3 in broken lines. As discussed above, microprocessor 62 can be coupled to a belt drive control 68 instead of or in addition to belt position transducers for determining the position of the cullet stream by advance of the conveyor.

Microprocessor 62 can also be coupled to control the microwave heating unit(s), for example to control the frequency or power level of their output or simply to turn them on and off. Likewise the microprocessor can monitor other aspects of operation of the invention such as the heating and detection path velocity, heating and detecting layer depth and the like. For operator interface, a keypad and display device can be included. The operator interface is useful to permit selection of pass/divert criteria, to alter operation of the sorting apparatus for job changes, to collect selection information and other management information, etc.

Figure 5:
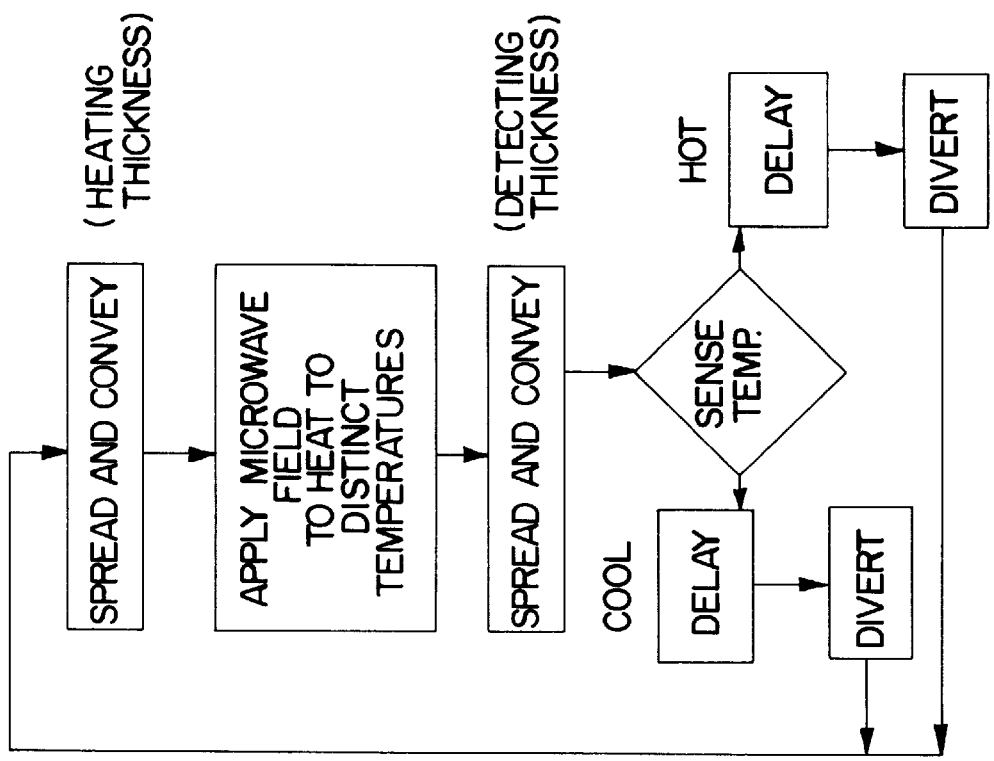
FIG. 5 is a flow chart showing the method steps employed according to the invention for sorting cullet.

FIG. 5 is a flow chart demonstrating the method employed according to the invention for sorting cullet. As described above, the method includes spreading the glass cullet with a heating layer thickness for presentation to the heating device, spreading the heated cullet with a detecting layer thickness, and conveying for presentation to the temperature measurement device. The cullet is conveyed along a heating path where microwave energy is applied at least at one frequency in a range of 0.915 to 2.450 GHz, and preferably at a relatively low single frequency (i.e., 0.915 GHz). This combination of heating layer thickness and low frequency microwave energy provides a cost effective way to heat contaminants for detecting different temperatures between glass particles and contaminant particles in the cullet.

Downstream of the heating area, along the detecting path, the resulting temperatures of the fragments of glass and the fragments of contaminants are stored at least as to incremental longitudinal lanes and preferably also lateral lengths of the cullet stream. As the conveyor advances to bring a given area of cullet before a diverting mechanism further downstream along the detecting path, one or more diverting mechanisms is operated for diverting the contaminants from the detecting path as a function of the sensed temperatures (i.e., contaminants are either hotter or cooler than the average temperature). FIG. 5 shows a delay provided to for travel time of the detected contaminants from the temperature sensor to the diverting mechanisms.

Figure 6:
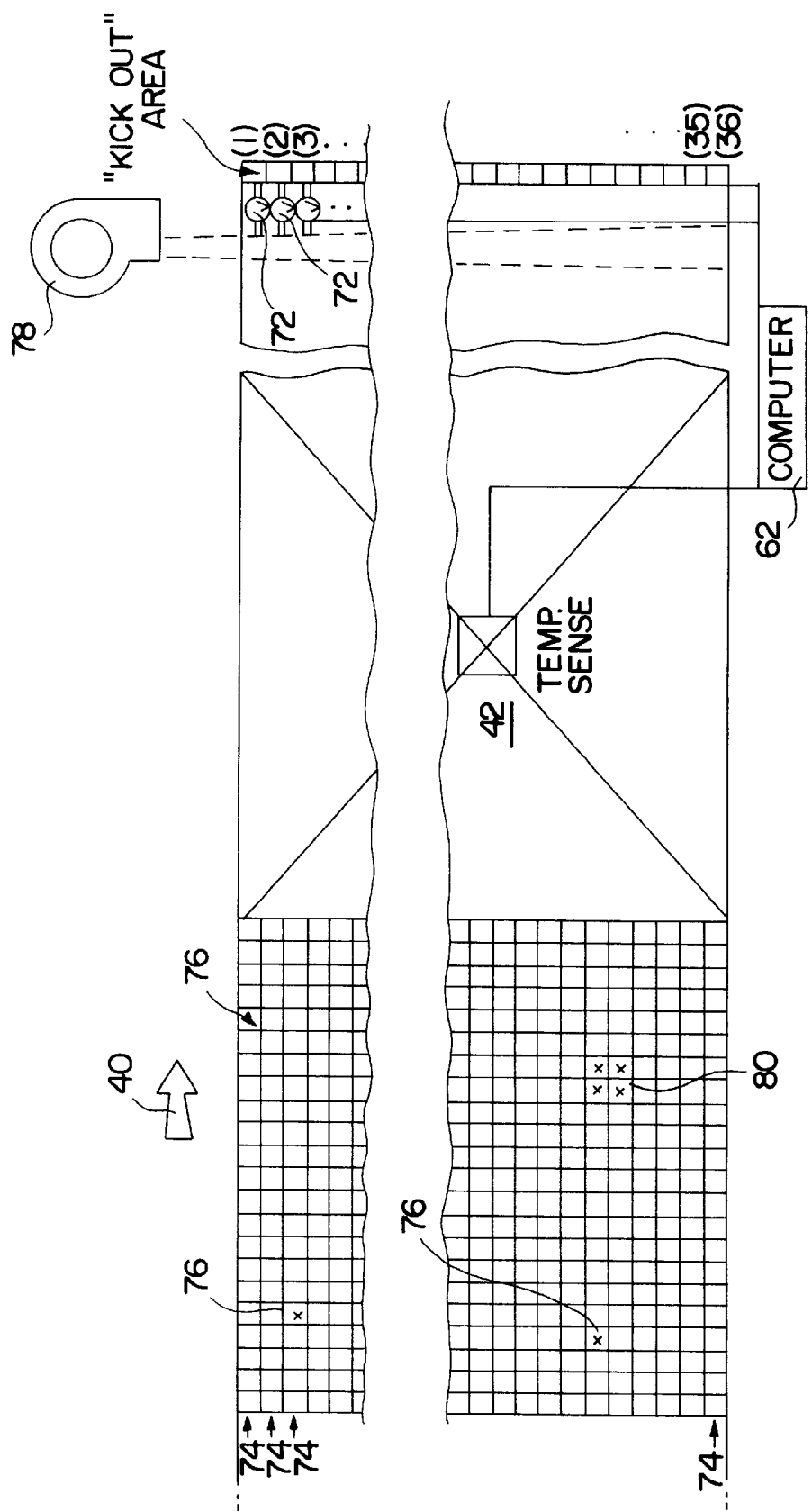
FIG. 6 is a perspective view showing a sensor and air driven diverter arrangement for discriminating an X-Y matrix of cullet for contaminants therein.

FIG. 6 demonstrates the invention with respect to the a plurality of areas divertable in a plurality of distinct lanes 74 and lateral lengths thereby forming an X-Y matrix of discrete areas 76 of the conveyor that are divertable. The detected temperature of a contaminated area deviates from the average due to the thermal characteristics of one or more contaminant particles in the corresponding area of the cullet stream. The average temperature of a section with contaminants may be, for example, several degrees Fahrenheit different than uncontaminated adjacent areas; and the difference in temperatures between individual particles of glass vs. contaminant is typically six to twelve degrees different. Diverters capable of removing the area of the contaminants are operated in a corresponding discrete fashion to remove all the cullet in the area of each contaminant, which removed cullet can be reprocessed to further separate or concentrate the glass and the contaminants. FIG. 6 shows a schematic representation of thirty-six individual diverters or solenoid valves 72 which each define a distinct lane in which cullet material is divertable over an incremental length of the material stream (the distinct lanes are shown numbered in brackets). The solenoid valves are coupled to a compressed air source 78 and are controlled by microprocessor 62. Each solenoid valve 72 is operated in a pulsed fashion allowing a relatively short burst of air to flow through the solenoid valve and divert a discrete area 76 in one of the distinct lanes 74. The duration of the burst of air defines the longitudinal length of material in the discrete lane which is diverted (i.e., a longer durst duration equates to a longer diverted length).

Detected contaminants can be potentially appear in a cluster which spans more than discrete area. FIG. 6 shows a larger discrete area 80 spanning several adjacent discrete areas. The system is operable to actuate the corresponding pair diverters with a sufficient air burst duration to completely remove the larger discrete area 80. Similarly, the system is operable to actuate any number of diverters for the appropriate air burst duration to divert all discrete areas in which contamination is detected.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:

1. Method for separating a stream of mixed particulates of at least two distinct materials having at least one of different thermal, dielectric strength and loss tangent characteristics, comprising:

providing a conveying means having a heating path followed by a detecting path;

spreading a heating layer of mixed particulates, having a heating layer thickness, along the heating path;

heating the heating layer to an exit temperature with an electromagnetic induction heater disposed along the heating path, the electromagnetic induction heater being operable to apply an electromagnetic field to heat the heating layer;

spreading the heating layer along the detecting path thereby forming a detecting layer having a detecting layer thickness, the heating layer thickness being larger than the detecting layer thickness;

detecting and signaling a difference in temperature between the two distinct materials in the detecting layer using a temperature sensor operable to detect and signal the difference in temperature between the two distinct materials occurring as a result of said different thermal characteristics;

diverting a portion of the detecting layer as a function of the difference in temperature, whereby the two materials are separated using at least one controllable diverting mechanism responsive to a signal of the temperature sensor for diverting a portion of the detecting layer.

2. The method of claim 1 comprising:

moving the heating layer along the heating path at a heating path velocity;

transferring the heating layer onto the detecting path moving at a detecting path velocity, the detecting path velocity being greater than the heating path velocity, thereby forming the detecting layer.

3. The method of claim 1 comprising heating the detecting path to at least the exit temperature.

4. The method of claim 2 wherein the detecting path velocity is 4.5 to 15.5 times greater than the heating path velocity.

5. The method of claim 2 wherein the heating path has a heating path width and the detecting path has a detecting path width, the heating path width and the detecting path width being equal.

6. The method of claim 5 wherein the detecting path velocity is 18 to 31 meters per minute and the heating path velocity is 2 to 4 meters per minute.

7. The method of claim 1 wherein the cullet is washed and dried prior to heating the heating layer with the electromagnetic induction heater, the cullet having a pre-heating temperature in the range of 60° C. to 82° C.

8. The method of claim 1 wherein the heating layer thickness is approximately 7.6 cm.

9. The method of claim 1 wherein the stream of mixed particles has an average particle size and the detecting layer thickness is approximately equal to the average particle size.

10. The method of claim 9 comprising:

moving the heating layer along the heating path at a heating path velocity;

transferring the heating layer onto the detecting path moving at a detecting path velocity thereby forming the detecting layer, the detecting path velocity being sufficiently greater than the heating path velocity so that the detecting layer thickness is approximately equal to the average particle size.

11. The method of claim 1 comprising:

detecting and signalling the difference in temperature of the detecting layer in a plurality of distinct lanes; and diverting a portion of the detecting layer as a function of the difference in temperature in each of the distinct lanes, whereby the two materials are separated using a controllable diverting mechanism for each distinct lane responsive to a signal of the temperature sensor for diverting a portion of the detecting layer.

12. The method of claim 11 wherein the difference in temperature of the detecting layer is detected in 30 to 36 distinct lanes.

13. The method of claim 1 wherein the induction heater comprises a broadband microwave generator and the electromagnetic field comprises microwaves in a frequency range of 0.915 to 2.45 GHz.

14. The method of claim 13, wherein the electromagnetic field includes a plurality of frequencies in said range.

15. An apparatus for separating a stream of mixed particulates of at least two distinct materials having at least one of different thermal, dielectric strength and loss tangent characteristics, comprising:

means operable to move the stream of mixed particulates along a heating path and a detecting path;

means for spreading a heating layer of mixed particulates, having a heating layer thickness, along the heating path;

an electromagnetic induction heater disposed along the heating path and operable to apply an electromagnetic field to heat the heating layer to an exit temperature;

means for spreading the heating layer onto the detecting path thereby forming a detecting layer having a detecting layer thickness, the heating layer thickness being larger than the detecting layer thickness;

at least one temperature sensor operable to detect a temperature of particulates in the detecting layer at least at one discrete point along the detecting path, the temperature sensor being operable to detect and signal a difference in temperature between the two distinct materials occurring as a result of said different thermal characteristics; and, at least one diverting mechanism controllable responsive to a signal of the temperature sensor for diverting a portion of the detecting layer as a function of the difference in temperature, whereby the two materials are separated.

16. The apparatus of claim 15 wherein the conveying means has a heating path movable at a heating velocity and a detecting path movable at a detecting velocity the detecting path velocity being greater than the heating path velocity.

17. The apparatus of claim 16 wherein the detecting path and the heating path are belt driven conveyors.

18. The apparatus of claim 16 wherein the means for spreading the heating layer along the heating conveyor path is a cullet rake.

19. The apparatus of claim 16 wherein the detecting layer has an average particle size and the heating path has an end located above the detecting path and the heating layer is dropped from the end of the heating path onto the detecting path thereby forming the detecting layer having a detecting layer thickness which is approximately equal to the average particle size.

20. The apparatus of claim 15 wherein the detecting layer has an average particle size and the detecting path is a vibratory conveyer and the heating path transfers the heating layer onto the vibratory conveyor thereby forming the detecting layer having a detecting layer thickness which is approximately equal to the average particle size.

21. The apparatus of claim 15 comprising a means for heating the detecting path to at least the exit temperature.

22. The apparatus of claim 15 wherein the temperature sensor is an infrared imaging camera operating in the 3 $\mu$m to 12 $\mu$m range.

23. The apparatus of claim 22 wherein the infrared camera is operable to process image data representing the relative temperature of at least a portion of the detecting layer with a resolution of 320×240 pixels and a frame rate of 30 frames per second.

24. The apparatus of claim 22 comprising a digital processor operable to process the image data such that detecting layer is divided into a plurality of lanes, the processor being operable to generate a signal for diverting a portion of the detecting layer as a function of the difference in temperature between successive frames of data for each individual lane.

* * * * *